United States Patent
Roessl et al.

(10) Patent No.: US 9,168,013 B2
(45) Date of Patent: Oct. 27, 2015

(54) BREAST DENSITY ASSESSMENT

(75) Inventors: Ewald Roessl, Ellerau (DE);
Hanns-Ingo Maack, Norderstedt (DE);
Klaus Erhard, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 114 days.

(21) Appl. No.: 13/991,923

(22) PCT Filed: Dec. 8, 2011

(86) PCT No.: PCT/IB2011/055548
§ 371 (c)(1),
(2), (4) Date: Jun. 6, 2013

(87) PCT Pub. No.: WO2012/080914
PCT Pub. Date: Jun. 21, 2012

(65) Prior Publication Data
US 2013/0251104 A1 Sep. 26, 2013

(30) Foreign Application Priority Data

Dec. 13, 2010 (EP) ..................................... 10194750

(51) Int. Cl.
*A61B 6/00* (2006.01)

(52) U.S. Cl.
CPC . *A61B 6/502* (2013.01); *A61B 6/00* (2013.01); *A61B 6/482* (2013.01); *A61B 6/488* (2013.01); *A61B 6/542* (2013.01)

(58) Field of Classification Search
CPC ........ A61B 6/502; A61B 6/0412; A61B 6/06;
A61B 6/4233; A61B 6/0431; A61B 6/00;
A61B 6/482; A61B 6/488; A61B 6/542;
A61B 6/025; A61B 6/0414; A61B 6/5247;
A61B 8/0825; A61B 8/403; A61B 8/4416;
A61B 8/483; A61B 8/5261; A61B 6/4258;
A61B 6/037; A61B 6/4488; A61B 6/4028;
A61B 6/583; A61B 6/4291; A61B 6/548;
A61B 6/032; A61B 6/484; A61B 6/563;
A61B 6/40; Y10T 29/49002
USPC ............................. 378/37, 62, 4, 9; 382/132
See application file for complete search history.

(56) References Cited

U.S. PATENT DOCUMENTS 7,756,242 B2 7/2010 Kudo
8,115,784 B2 * 2/2012 Licato et al. .................. 345/634
(Continued)

FOREIGN PATENT DOCUMENTS

EP 1216661 6/2002
EP 1426903 6/2004

OTHER PUBLICATIONS

Hammer, Mark, "X-Ray Physics: X-Ray Interaction With Matter and Attenuation" (2014), http://www.xrayphysics.com/attenuation.html, pp. 1-9.
(Continued)

*Primary Examiner* — Irakli Kiknadze

(57) ABSTRACT

The present invention relates to mammography. To provide breast density assessment with improved accuracy in the results, a method (100) is proposed for providing mammography information about an object of interest, the region of interest comprising a tissue structure, with the following steps: a) acquiring (110) first image data (112) with first image acquisition parameters (114), wherein the first image parameters are adapted to a first radiation spectrum of a dual energy mode; and wherein the first image acquisition is performed with a low X-ray dosage of a pre-scan; b) acquiring (116) second image data (118) with second image acquisition parameters (120), wherein the second image parameters are adapted to a second radiation spectrum of the dual energy mode, and wherein the second image acquisition is performed with a higher X-ray dosage than the first image acquisition, and wherein the second image acquisition is a Mammography scan; c) performing (122) a dual energy basis material decomposition (124) based on the first and second image data to generate decomposed basis material image data (126); and d) deriving (128) a density information (130) of the tissue structure of the region of interest from the decomposed basis material image data; and providing (132) the density information to a user.

20 Claims, 8 Drawing Sheets

(56) References Cited

U.S. PATENT DOCUMENTS

| | | |
|---|---|---|
| 2005/0069086 A1 | 3/2005 | Deych et al. |
| 2007/0165781 A1 | 7/2007 | Aslund |
| 2007/0211859 A1* | 9/2007 | Okada et al. .................. 378/97 |
| 2009/0022273 A1 | 1/2009 | Kashiwagi et al. |
| 2010/0135456 A1 | 6/2010 | Jing et al. |
| 2010/0226475 A1 | 9/2010 | Smith et al. |

OTHER PUBLICATIONS

Basic Physics of Digital Radiography/The Patient, Wikibooks (2014), Fig. 3.6, http://en.wikibooks.org/wiki/basic_physics_of_digital_radiography/the_patient, pp. 1-76.

Basic Physics of Digital Radiography/The Source, Wikibooks (2014), Fig. 2.9, http://en.wikibooks.org/wiki/basic_physics_of_digital_radiography/the_source, pp. 1-16.

* cited by examiner

BREAST DENSITY ASSESSMENT

FIELD OF THE INVENTION

The present invention relates to an X-ray imaging system, a method for providing mammography information about an object of interest, as well as a computer program element and a computer readable medium.

BACKGROUND OF THE INVENTION

Information about tissue structure is used for so-called cancer screenings, in particular in mammography. US 2009/0022273 A1 describes an X-ray system for mammography exposures. Further, it is known to acquire X-ray images in order to be able to make an assessment of volumetric breast density, which breast density is a key feature or a key characteristic, for detection and prediction of cancer such as breast cancer. However, it has been shown that the assessment of volumetric breast density from conventional mammograms may result in false predictions due to the influence of a 3D breast model estimation on the accuracy of the calculation.

SUMMARY OF THE INVENTION

It may be an object of the present invention to provide breast density assessment with improved accuracy in the results.

The object of the present invention is solved by the subject-matter of the independent claims, wherein further embodiments are incorporated in the dependent claims. It should be noted that the following described aspects of the invention apply also for the X-ray imaging system, the method for providing mammography information, the program element, and the computer readable medium.

According to an exemplary embodiment of the invention, a method for providing mammography information about an object of interest is provided, wherein the region of interest comprises a tissue structure, the method comprising the following steps:
a) Acquiring first image data with first image acquisition parameters, wherein the first image parameters are adapted to a first radiation spectrum of a dual energy mode, and wherein the first image acquisition is performed with a low X-ray dosage of a pre-scan;
b) Acquiring second image data with second image acquisition parameters, wherein the second image parameters are adapted to a second radiation spectrum of the dual energy mode, and wherein the second image acquisition is performed with a higher X-ray dosage than the first image acquisition, and wherein the second image acquisition is a mammography scan;
c) Performing a dual energy basis material decomposition based on the first and second image data to generate decomposed basis material image data; and
d) Deriving density information of the tissue structure of the region of interest from the decomposed basis material image data, and providing the density information to a user.

It must be noted that the terms "first" and "second" are used to differentiate between different features of the same kind, like "first dose" and "second dose". However, the terms "first" and "second" do not automatically relate to any (temporal) order, except where this is mentioned or can be derived from the context.

According to an exemplary embodiment, step a) is performed before step b). In other words, a pre-scan is performed before a main scan.

According to an alternative embodiment, step b) is performed before step a), i.e. a scan is performed with a high dose and another scan is done thereafter with a low dose.

According to a further exemplary embodiment, the dual energy basis material decomposition separates image data relating to a first tissue type from image data relating to a second tissue type.

According to a further exemplary embodiment, the decomposed basis material image data is provided to the user.

According to a further exemplary embodiment, in a further step f), display data is generated based on the second image data, wherein the image data is provided as a mammography image to a user.

According to a further exemplary embodiment, the first image data and the second image data are combined to generate display data to be presented to the user.

According to a further exemplary embodiment, an X-ray imaging system is provided, comprising an X-ray image acquisition device with an X-ray source and X-ray detector, a processing unit, and an interface unit. The X-ray image acquisition device is adapted to acquire first image data with first image acquisition parameters, wherein the first image parameters are adapted to a first radiation spectrum of the dual energy mode. The X-ray image acquisition device is adapted to perform the first image acquisition with a low X-ray dosage of a pre-scan. The X-ray image acquisition device is further adapted to acquire second image data with second image acquisition parameters, wherein the second image parameters are adapted to a second radiation spectrum of the dual energy mode. The X-ray image acquisition device is also adapted to perform the second image acquisition with a higher X-ray dosage than the first image acquisition. The second image acquisition is a mammography scan. The processing unit is adapted to perform a dual energy basis material decomposition based on the first and second image data to generate decomposed basis material image data, and to derive density information of the tissue structure of the region of interest from the decomposed basis material image data. The interface unit is adapted to provide the density information to a user.

It can be seen as the gist of the invention to use a pre-scan performed prior to a clinical mammographic scan, which pre-scan is done at low dose. The pre-scan is then used together with the mammography scan for a dual energy basis material decomposition to estimate density information of the tissue structure, for example the breast tissue structure.

These and other aspects of the present invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
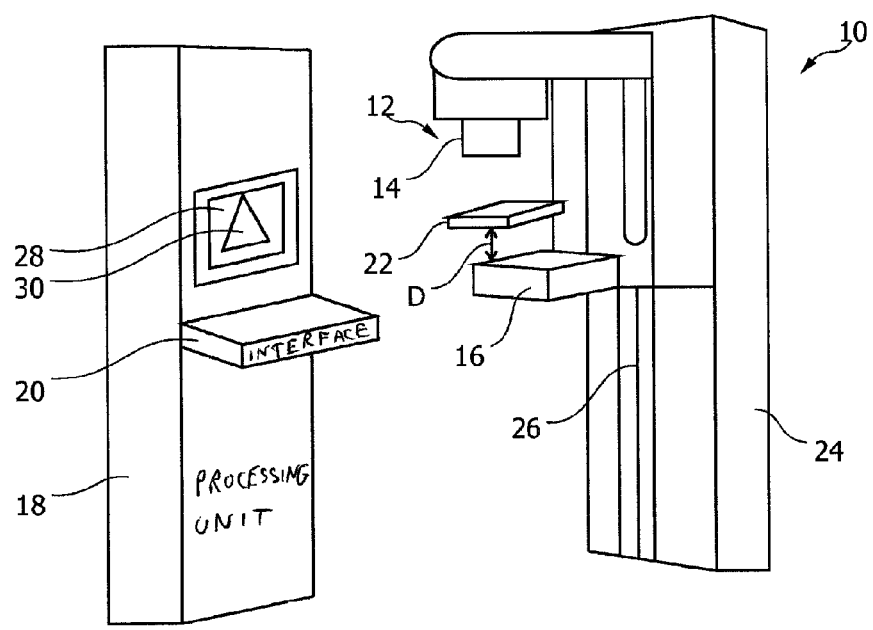
FIG. 1 illustrates an X-ray imaging system according to an exemplary embodiment of the invention.

FIG. 1 shows an X-ray imaging system 10 comprising an X-ray image acquisition device 12 with an X-ray source 14 and an X-ray detector 16. Further, a processing unit 18 and an interface unit 20 are provided.

The X-ray imaging system 10 shown is a mammography system where a patient can stand in an upright position, wherein a breast of the patient, or any other part of the body, at least theoretically, can be provided between the X-ray source 14 and the X-ray detector 16. To hold the breast in place during the acquisition procedure, a first panel 22 is shown. By moving the first panel upwards or downwards, the distance between the panel and the detector, indicated with reference D, can be adapted to the respective size of the breast. Thus, a desired pressure can be acted upon the breast for a proper acquisition procedure.

The detector 16 is also formed as a sort of panel having a surface area upon which the breast can be received.

As indicated, the X-ray image acquisition device is movably supported to a support structure 24, which comprises an adjusting mechanism 26, indicated by a vertical post. Thus, the X-ray image acquisition device 12 can be moved upwards or downwards to be adapted to the patient's height, such that the patient can stand in a comfortable position during the acquisition procedure.

The X-ray image acquisition device 12 is adapted to acquire first image data with first image acquisition parameters, wherein the first image parameters are adapted to a first radiation spectrum of the dual energy mode. The X-ray image acquisition device is further adapted to perform the first image acquisition with a low X-ray dosage of a pre-scan.

The X-ray image acquisition device 12 is further adapted to acquire second image data with second image acquisition parameters, wherein the second image parameters are adapted to a second radiation spectrum of the dual energy mode. The X-ray image acquisition device is adapted to perform the second image acquisition with a higher X-ray dosage than the first image acquisition. The second image acquisition is a mammography scan.

The processing unit, which is of course connected to the X-ray image acquisition device, however the connection is not further shown, is adapted to perform a dual energy basis material decomposition based on the first and second image data to generate decomposed basis material image data; and to derive a density information of the tissue structure of the region of interest from the decomposed basis material image data. Further, the interface unit is adapted to provide the density information to a user. It must be noted that the interface unit 20 is not further shown.

According to an exemplary embodiment of the invention, a display device 28 is provided, wherein the display device is connected to the processing unit 18. The display device is adapted to display density information to the user, which density information is indicated with reference numeral 30.

It is explicitly noted that the X-ray imaging system 10 of FIG. 1 can be equipped with the display device 28; however it is not necessary that the display device is provided according to an exemplary embodiment of the invention. In other words, the features described above can also be taken without the combination of the display device.

It is further noted that other X-ray imaging systems are also provided according to the invention, but not shown in the figures. For example, any X-ray system with fixed source and detector can be used. Further, also other systems suited for mammography are provided, such as C-arm systems. It is of course also possible to provide systems where a table is provided to receive a patient which can be arranged facing downwards for mammography scans.

According to a further exemplary embodiment (not further shown), the processing unit 18 is adapted to generate display data based on the second image data, wherein the display device is adapted to display the image data as a mammography image.

In the following, different exemplary embodiments of a method according to the invention for providing mammography information about an object of interest are described.

Figure 2:
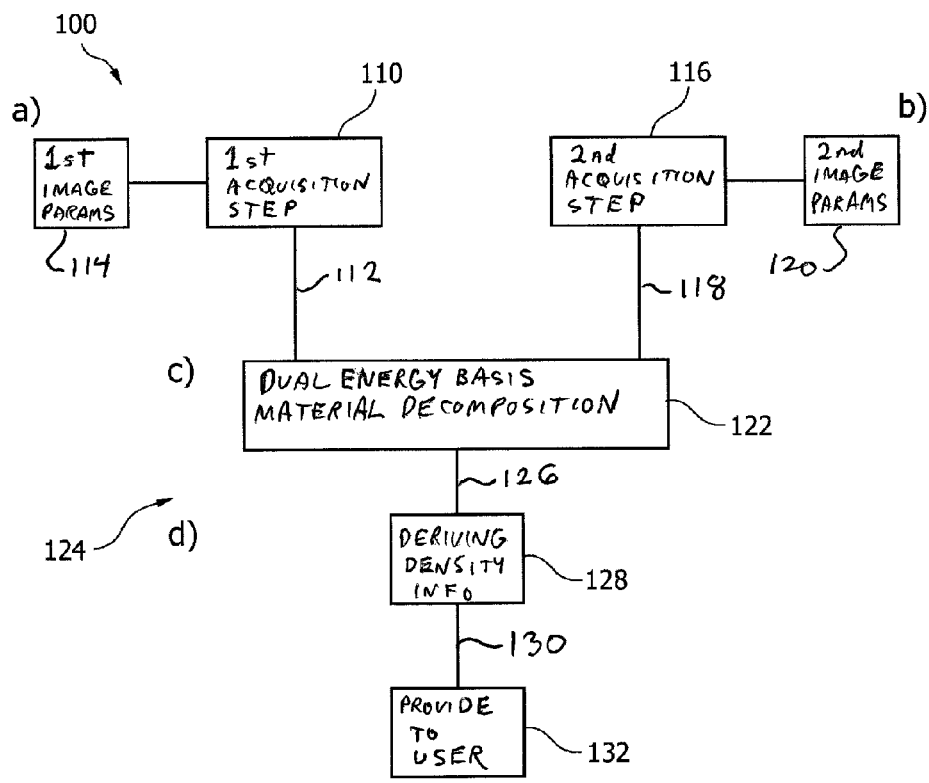
FIG. 2 illustrates basic steps of an exemplary embodiment of a method of the invention.

In FIG. 2, a method 100 for providing mammography information about an object of interest is shown, wherein the region of interest comprises a tissue structure. The method comprises the following steps:

In a first acquisition step 110, first image data 112 is acquired with first image acquisition parameters 114. The first image parameters 114 are adapted to a first radiation spectrum of a dual energy mode. The first image acquisition is performed with a low X-ray dosage of a pre-scan.

In a second acquisition step 116, second image data 118 is acquired with second image acquisition parameters 120. The second image parameters are adapted to a second radiation spectrum of the dual energy mode. The second image acquisition is performed with a higher X-ray dosage than the first image acquisition. The second image acquisition is a mammography scan.

Further, in a performance step 124, a dual energy basis material decomposition 122 is performed based on the first and second image data to generate decomposed basis material image data 126.

Furthermore, in a deriving step 128, density information 130 of the tissue structure of the region of interest is derived from the decomposed basis material image data 126. The density information is then provided to a user, indicated with reference numeral 132.

The first acquisition step 110 is also referred to as step a), the second acquisition step 116 is also referred to as step b), the performing step 124 is also referred to as step c), and the deriving step 128 is also referred to as step d).

According to the exemplary embodiment shown in FIG. 2, step a) is performed before step b). In other words, step a) is a pre-scan and step b) is a main scan.

According to an alternative embodiment (not further shown), step b) is performed before step a), i.e. a first scan is performed with a high does and a second scan is done thereafter with a low dose.

According to a further aspect of the invention, the density information comprises a density value.

According to a further aspect, the density value is an average density value of the region of interest.

According to a further aspect, the density value is a density value of the region of interest for different tissue types.

According to a further exemplary embodiment, not shown, a first radiation dose is applied during the first image acquisition and a second radiation dose during the second acquisition. The first dose is smaller than the second dose at least by a factor of 2. In other words, the first dose is approximately less than 50% of the second dose, or approximately 50% of the second dose or less, or at most 50% of the second dose.

According to a further aspect, the first dose is at least less than 20% of the second dose, preferably less than 10%.

According to an exemplary embodiment, not shown, the first dose is at most 5% of the second dose, preferably less. For example, the dose of the first scan is 2.5% of the second scan.

Of course, in case of the above mentioned alternative exemplary embodiment with a scan with high dose performed before scan with a low dose, the dose rate is applied in a reversed manner, respectively, i.e. the scan performed before the other one has a dose that is larger than the dose of the scan performed after that at least by a factor of 2. In other words, the dose of the scan performed before the other one, is approximately more than 200% of dose of the scan performed afterwards.

According to a further exemplary embodiment, not further shown, the first and second radiation spectra exhibit minimal spectral overlap. For example, they are separated from each other. In other words, the x-ray spectra corresponding to the first and second radiation spectra exhibit the least possible overlap on the energy axis. For example, this can be achieved by employing appropriate combinations of kVp values and filter materials.

In particular, according to an exemplary embodiment, the high-kVP scan, preferably the pre-scan should be heavily filtered to (a) reduce the dose as required and (b) reduce the spectral overlap.

Figure 3:
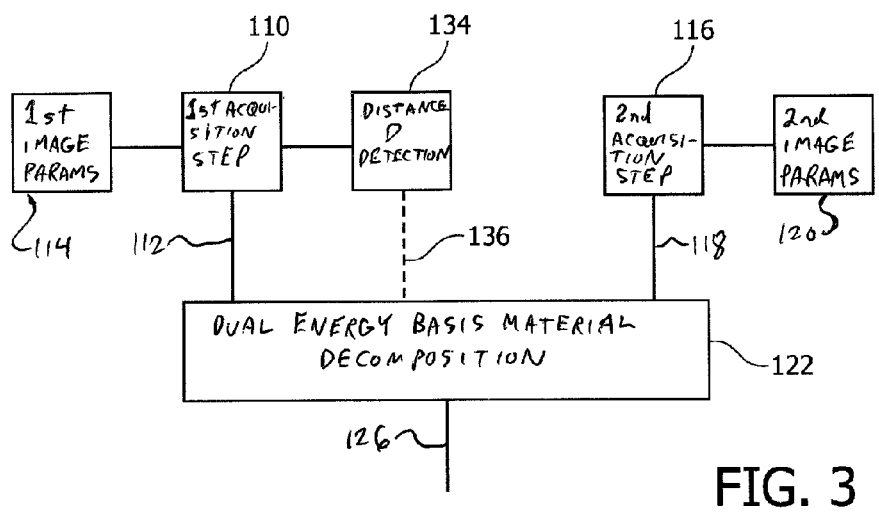
FIG. 3 shows a further exemplary embodiment of the method according to the invention.

According to a further exemplary embodiment, shown in FIG. 3, in step a), the region of interest is arranged between two compression elements and the distance D between the two compression elements is detected by a distance measuring sensor. The detection is indicated with a further box 134, comprising the reference numeral D inside for the distance.

According to a further aspect, the thickness of the region of interest that can be derived by the distance D detected in step 134 is determined for performing step c), which is indicated by a dotted line 136 connecting the box 134 with the box 122.

According to a further exemplary embodiment, although not further shown, in step c), the dual energy basis material decomposition separates image data relating to a first tissue type from image data relating to a second tissue type.

According to a further aspect, the first tissue type is glandular tissue and the second tissue type is adipose tissue.

According to a further aspect, a first density value for glandular tissue and a second density value for the adipose tissue are provided. Of course, the density values can also be provided as density information.

According to the invention, the term "density information" comprises different types of data providing the desired density information, such as, a rather simple form, a single number or value, a pair of values, a graphical representation in form of a two-dimensional graph or even three-dimensional image data from which the density information can be derived by the user.

According to a further aspect, in step c), mean values for glandular tissue and for adipose tissue are determined.

According to a further aspect, mean values for the first and second tissue type for a selectable region are determined and provided to the user. Thus, the user, for example a clinical staff member, can indicate a region of particular interest, i.e. he can select a certain region of interest which can be smaller than the region of interest to which the term of image acquisition refers to, such that he is provided with means values for the particular selected region.

According to a further aspect, a section or part of the breast can be selected.

According to a further aspect, the whole breast can be selected.

Figure 4:
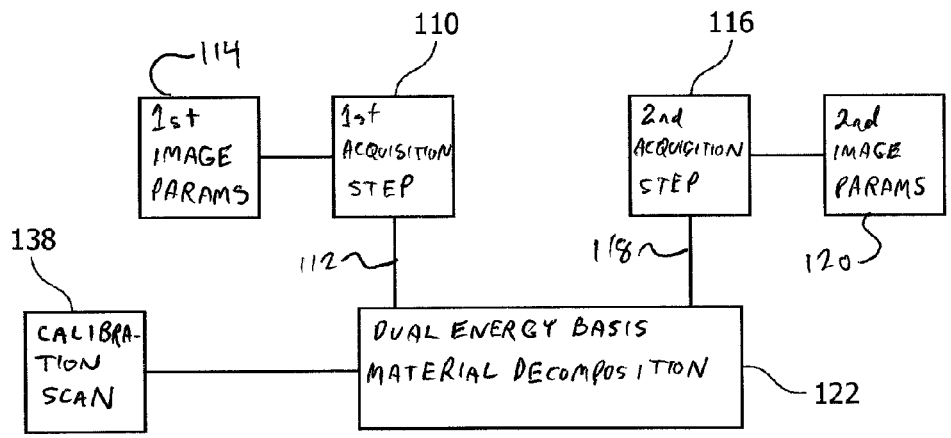
FIG. 4 shows a further exemplary embodiment of a method according to the invention.

According to a further exemplary embodiment, shown in FIG. 4, the decomposition is based on calibration data 136 which is acquired in a calibration scan 138, for example before performing the above described method steps according to one of the described exemplary embodiments.

According to a further aspect, the first and second image data in steps a) and b) are acquired with the same first and second spectra as the calibration scan (not further shown).

Figure 5:
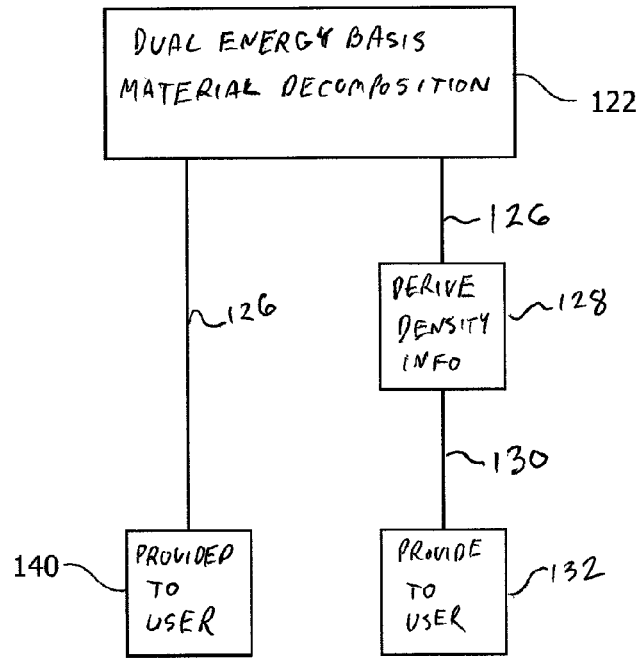
FIG. 5 shows a further exemplary embodiment of a method according to the invention.

According to a further exemplary embodiment, shown in FIG. 5, the decomposed basis material image data 126 is provided to the user, indicated with a box 140. Thus, the user is not only provided with density information 130, as indicated by the provision box 132, but also with the decomposed basis material image data.

According to a further aspect, decomposed image display data is derived from the decomposed basis material image data in order to display a respective image.

Figure 6:
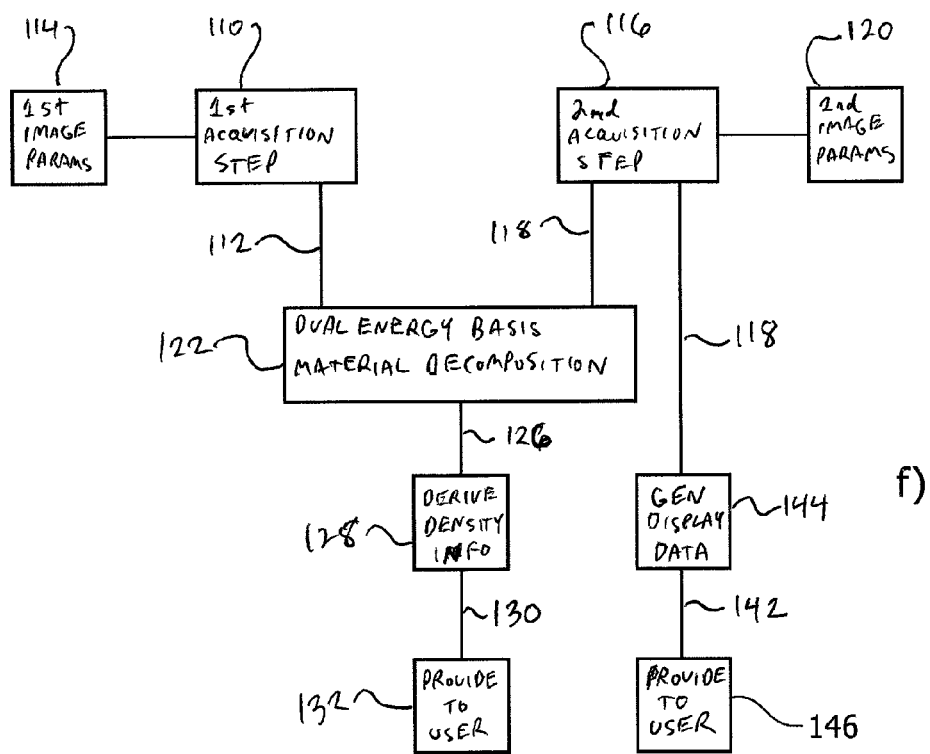
FIG. 6 shows a further exemplary embodiment of a method according to the invention.

According to a further exemplary embodiment, shown in FIG. 6, in a further step f), display data 142 is generated in a generation step 144 based on the second image data. The display data 142 is provided in a provision step 146 to the user as a mammography image 148.

According to a further aspect, the second image acquisition is referred to as a main mammography acquisition.

According to a further aspect, the second image acquisition is a diagnostic scan providing sufficient information for a clinical staff member or other personnel to derive the respective diagnostic assessments.

Figure 7:
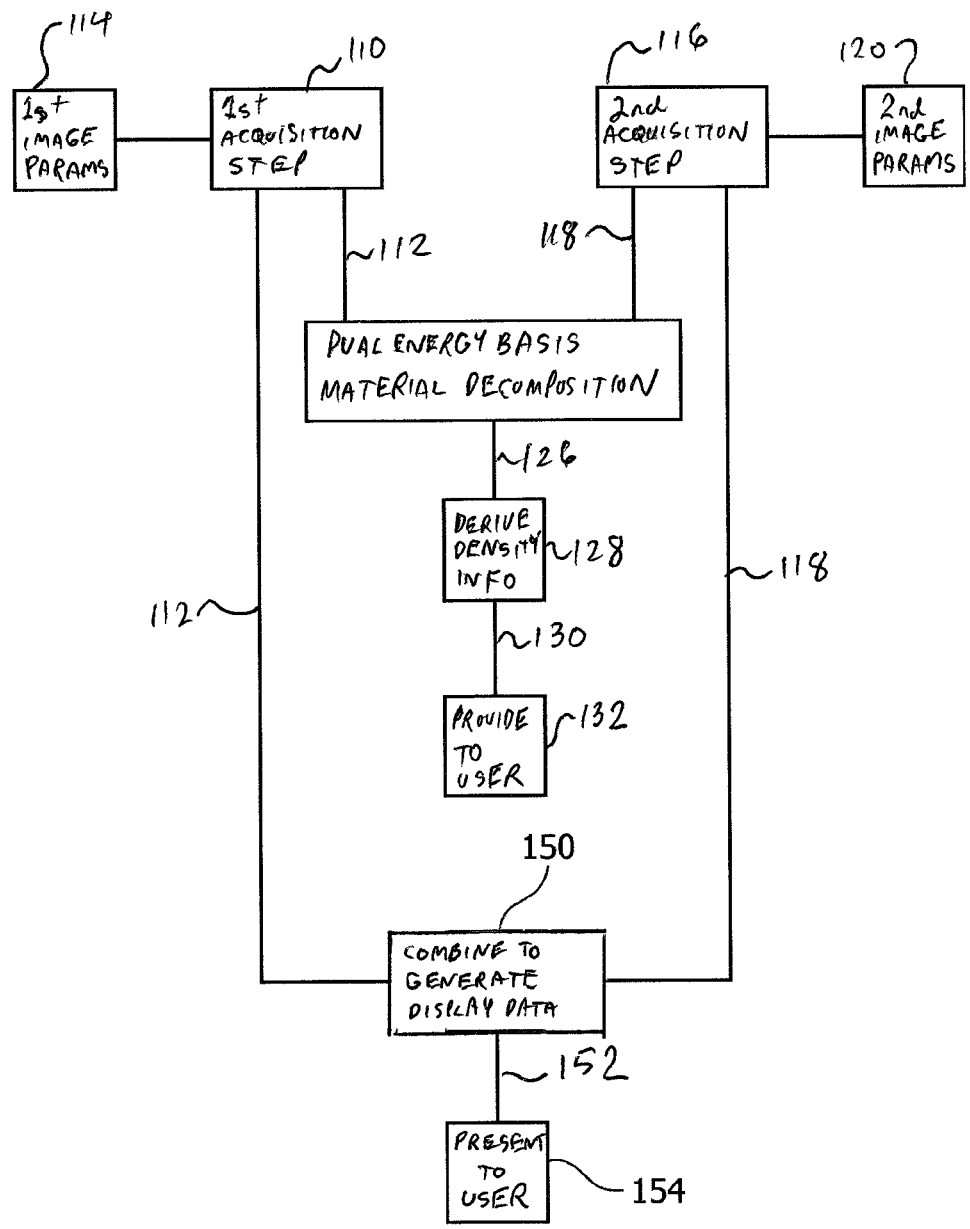
FIG. 7 shows a further exemplary embodiment of a method according to the invention.

According to a further exemplary embodiment, shown in FIG. 7, the first image data 112 and the second image data 118 are combined in a combination step 150 to generate display data 152 to be presented to the user, which is indicated by a box 154.

Figure 8:
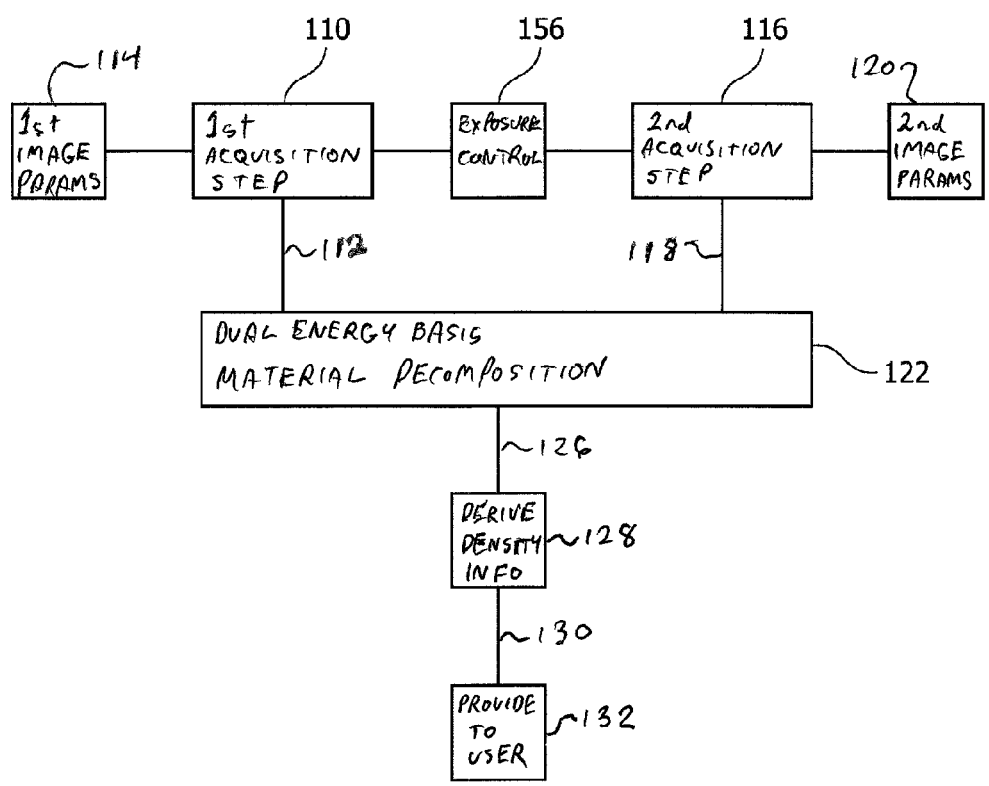
FIG. 8 shows a further exemplary embodiment of a method according to the invention.

According to a further exemplary embodiment, which is schematically shown in FIG. 8, the first image data of step a) is used for an exposure control 156 in step b).

It is explicitly noted that the above described exemplary embodiments can be combined in various ways which leads to synergetic effects which are not further described.

According to a further aspect, it is an essential idea to utilize a pre-scan performed prior to the clinical mammographic scan used, for example, for correct positioning of the breast. The pre-scan is done at a low dosage and the kVp can be set different from kVp setting during the main scan without compromising the positioning. It is an aspect of the invention to perform a dual energy basis material decomposition into, for example, the glandular tissue/adipose tissue basis and to estimate the breast density on the entire mammogram based on a decomposition.

Of course, it is also possible to estimate the breast density for only a selected region of the mammogram.

Despite the fact that material decomposition is very noisy due to the low dose employed in the pre-scan and the noise-amplification effect due to the decomposition itself, the estimate of the breast density is hardly affected by this noise, since all the data achieved is used in an additive manner, for example, to compute a single number.

It is further noted that the assessment of volumetric breast density from conventional mammograms may have several disadvantages. Despite the fact that the known distance between the two panels holding the breast, allows a decomposition of the attenuation into attenuation caused by adipose and glandular tissue, this does not always work for the boundaries where the breast does not fully touch the panels, i.e., the thickness of breast which the X-rays pass is smaller than the panel distance. This may lead to artefacts that influence the accuracy of the calculation of the average density of the breast.

The above described exemplary embodiments of the invention provide an alternative and improved way to compute breast density by making use of a low dose pre-scan in combination with the main mammographic acquisition.

One of the aspects of the invention is to remove the bias in the estimation of the average breast density assessment resulting from the high intensity regions on the mammogram where the thickness of the exposed tissue is small. It is noted that usually algorithms tend to interpret these regions as having a high fraction of adipose tissue. Thus, errors can occur in form of over- or under-estimation. It is further noted that also methods to account for the precise form of the breast in those regions can at best be considered approximations of the true form of the breast and will not lead to unbiased answers.

In the following, a simulation shall be illustrated, the dual energy separation and the following breast density assessments in the case of a 24 kVp/150 mAs diagnostic scan and a 35 kVp pre-scan with variable tube loadings of 1 mAs, 5 mAs, 10 mAs and 150 mAs.

Figure 9:
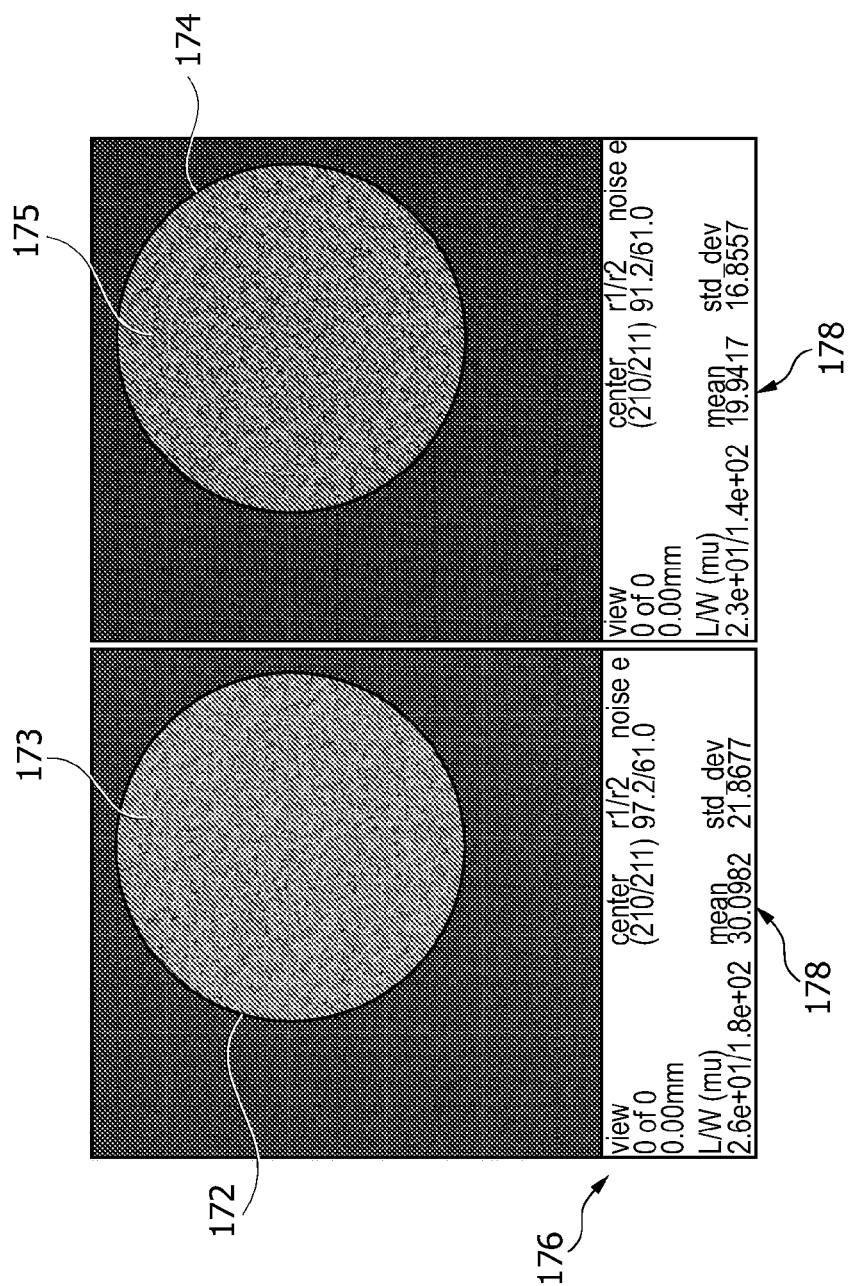
FIG. 9 shows an exemplary embodiment of decomposed basis material image data provided to the user according to the invention.

As a phantom, two cylindrical slabs of adipose tissue and glandular tissue of the same diameter are used with thicknesses of 30 mm and 20 mm, respectively. The decomposition into the two tissue types is illustrated in FIG. 9 in the case of the 10 mAs case of the tube loading for the pre-scan. The left part of FIG. 9 shows a decomposition of the dual energy data into adipose tissue ICRU44. As can be seen, the thus derived image data is shown in form of a circular area 172. The shape of the area results from the shape of the chosen cylindrical slab. However, the circle 172 is filled with a certain pixel pattern, i.e. a first pattern 173, indicating the respective density image data.

FIG. 9 shows in the right part a breast tissue ICRU44 which is glandular tissue structure, also indicated with a second circular area 174. The circle 174 is filled with a second pattern 175, which second pattern indicates the respective density image data for the respective tissue type.

Both representations are for the case of the 10 mAs tube loading of the 35 kVp pre-scan.

Further, below the image representation, further information 176 is presented. For example, a mean value 178 is presented for each of the tissue types.

From the mean values in the images of FIG. 9, it can be seen that on average the length of X-rays through the two discs can be reconstructed with high precision despite the fact that the noise in the decomposed images is very high. Concerning the precision, it is noted that the mean value of the left part of FIG. 9 indicates 30.0982 and relates to 30 mm of adipose tissue, whereas in the right part of FIG. 9 the mean value is indicated with 19.9417, referring to 20 mm of glandular tissue.

Figure 10:
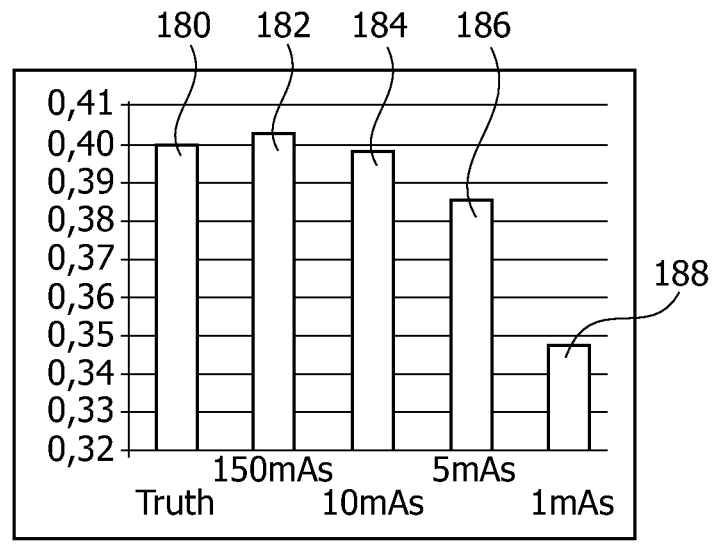
FIG. 10 shows a table describing accuracy aspects of breast density assessment for different dosages used for the pre-scan according to an exemplary embodiment of the invention.

As a further aspect, in FIG. 10 the results of the volumetric breast density measurements from respective projection data sets as shown in FIG. 9 as an example for the respective settings, are illustrated.

In FIG. 10, the fraction of glandular tissue, as an indicator for breast density usually referred to, is indicated on the vertical axis, starting with the value of 0.32 up to 0.42. On the horizontal axis, different cases are indicated.

As a first case, the truth is indicated with a first indicator 180, namely the relation of 20 mm of a total of 50 mm, which results in a fraction value of 0.4.

In a first simulation, a pre-scan has been performed with the same tube loading as the main scan, namely 150 mAs.

As can be seen by a second indicator 182, the result leads to a slightly increased value above the truth.

In a second simulation, a tube loading of 10 mAs has been applied, which is approximately 6.7% of a main tube loading at 150 mAs. A third indicator 184 leads up to nearly 0.4, thus indicating a rather accurate result.

Further, in a third simulation, a tube loading of 5 mAs has been applied, which is approximately 3.7% of a main scan of 150 mAs tube loading. A fourth indicator 186 leads up to a value, i.e. a fraction, of nearly 0.39.

In a fourth simulation, a tube loading of 1 mAs has been applied, which is approximately 0.7% of a 150 mAs tube loading. As can be seen by a fifth indicator 188, this leads to a value of 0.35 for the fraction of glandular tissue.

As can be seen already from the results in FIG. 10, using a pre-scan with about 5% of tube loading compared with the main tube loading of 150 mAs, leads to a rather good result.

Figure 11:
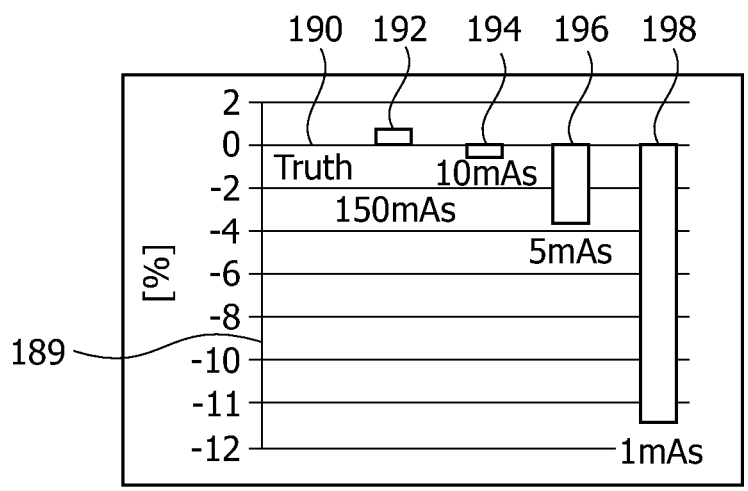
FIG. 11 shows an error bias for the results shown in FIG. 10.

In FIG. 11, the results from FIG. 10 are shown as a bias percentage 189 in the vertical axis. The vertical axis indicates a bias of −14% up to a bias of +2%.

Several indicators are shown starting from a line 190 indicating a value of 0% of the bias. Of course, in case of the truth, no indicator is shown. For the first simulation of a dosage of 100% of the main dosage, i.e. of 150 mAs for the pre-scan, a first arrow 192 leads up to nearly the value of 1%. A second indicator for the case of a 10 mAs pre-scan, which is referred to with reference numeral 194, has a negative bias of approximately 0.5%.

A third indicator 196 indicates the bias value in percent for the 5 mAs pre-scan version.

A fourth indicator 198 indicates an error bias of more than −12% for the case of a 1 mAs pre-scan.

As a result, a pre-scan of less than 10% tube loading, for example 10 mAs, instead of 150 mAs leads to a better result with respect to the error bias shown in FIG. 11. Even when applying only less than 5% of the dosage for a pre-scan, still a bias value of less than −4% can be achieved. This may depend on the particular way the measurement data is decomposed. For different procedures for the decomposition step, the results can thus be different. However, the quality with which the density information can be derived is the same though.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system comprising: an X-ray image acquisition device with an X-ray source and an X-ray detector; a processing unit; and an interface unit; wherein the X-ray image acquisition device is adapted to acquire first image data with first image acquisition parameters; wherein the first image parameters are adapted to a first radiation spectrum of a dual energy mode; and wherein the X-ray image acquisition device is adapted to perform the first image acquisition with a low X-ray dosage of a pre-scan; and wherein the X-ray image acquisition device is adapted to acquire second image data with second image acquisition parameters; wherein the second image parameters are adapted to a second radiation spectrum of the dual energy mode; and wherein the X-ray image acquisition device is adapted to perform the second image acquisition with a higher X-ray dosage than the first image acquisition, and wherein the second image acquisition is a mammography scan; wherein the processing unit is adapted to perform a dual energy basis material decomposition based on the first and second image data to generate decomposed basis material image data; and to derive a density information of the tissue structure of the region of interest from the decomposed basis material image data; and wherein the interface unit is adapted to provide the density information to a user.

2. The X-ray system of claim 1, wherein a display device is provided; and wherein the display device is connected to the processing unit; and wherein the display device is adapted to display density information; wherein the processing unit is adapted to generate display data based on the second image data; and wherein the display device is adapted to display the image data as a Mammography image.

3. The system of claim 1, wherein the first image acquisition is provided with a higher peak kilo-voltage (kVp) than the second image acquisition.

4. The system of claim 3, wherein the performing of the first image acquisition entails applying a first radiation dose and the performing of the second image acquisition entails applying a second radiation dose; wherein the first dose is at most 10% of the second dose.

5. A method for providing mammography information about an object of interest, the region of interest comprising a tissue structure, the method comprising the following steps: a) acquiring first image data with first image acquisition parameters; wherein the first image parameters are adapted to a first radiation spectrum of a dual energy mode; and wherein the first image acquisition is performed with a low X-ray dosage of a pre-scan; b) acquiring second image data with second image acquisition parameters; wherein the second image parameters are adapted to a second radiation spectrum of the dual energy mode; and wherein the second image acquisition is performed with a higher X-ray dosage than the first image acquisition, and wherein the second image acquisition is a mammography scan; c) performing a dual energy basis material decomposition based on the first and second image data to generate decomposed basis material image data; d) deriving a density information of the tissue structure of the region of interest from the decomposed basis material image data; and providing the density information to a user.

6. The method of claim 5, wherein step a) is performed before step b).

7. The method of claim 5, wherein a first radiation dose is applied during the first image acquisition and a second radiation dose during the second acquisition; wherein the first dose is smaller than the second dose at least by a factor 2.

8. The method of claim 5, wherein the first and second radiation spectra exhibit minimal spectral overlap.

9. The method of claim 5, wherein in step a) the region of interest is arranged between two compression elements and wherein the distance (D) between the two compression elements is detected by a distance measuring sensor.

10. The method of claim 5, wherein in step c) the dual energy basis material decomposition separates image data relating to a first tissue type from image data relating to a second tissue type.

11. The method of claim 5, wherein the decomposition is based on calibration data acquired in a calibration scan.

12. The method of claim 5, wherein the decomposed basis material image data is provided to the user.

13. The method of claim 5, wherein, in a further step f), display data is generated based on the second image data; and wherein the image data is provided as a mammography image to a user.

14. The method of claim 5, wherein the first image data and the second image data are combined to generate display data to be presented to the user.

15. The method of claim 5, wherein the first image data of step a) is used for an exposure control in step b).

16. The method of claim 5, wherein the first image acquisition is provided with a higher peak kilo-voltage (kVp) than the second image acquisition.

17. The method of claim 16, wherein performing of the first image acquisition entails applying a first radiation dose and performing of the second image acquisition entails applying a second radiation dose; wherein the first dose is at most 10% of the second dose.

18. A non-transitory readable medium embodying a computer program for providing mammography information about an object of interest, the region of interest comprising a tissue structure, said program having instructions executable by processor for performing a plurality of acts, from among said plurality there being the acts of: a) acquiring first image data with first image acquisition parameters; wherein the first image parameters are adapted to a first radiation spectrum of a dual energy mode; and wherein the first image acquisition is performed with a low X-ray dosage of a pre-scan; b) acquiring second image data with second image acquisition parameters; wherein the second image parameters are adapted to a second radiation spectrum of the dual energy mode; and wherein the second image acquisition is performed with a higher X-ray dosage than the first image acquisition, and wherein the second image acquisition is a mammography scan; c) performing a dual energy basis material decomposition based on the first and second image data to generate decomposed basis material image data d) deriving a density information of the tissue structure of the region of interest from the decomposed basis material image data and providing the density information to a user.

19. The computer readable medium of claim 18, wherein the first image acquisition is provided with a higher peak kilo-voltage (kVp) than the second image acquisition.

20. The computer readable medium of claim 19, wherein the acquiring of said first image data entails applying a first radiation dose and the acquiring of said second image data entails applying a second radiation dose; wherein the first dose is at most 10% of the second dose.

* * * * *